United States Patent [19]

Weiss

[11] 4,104,532
[45] Aug. 1, 1978

[54] DENTAL AND MEDICAL X-RAY APPARATUS

[75] Inventor: Mortimer E. Weiss, Laguna Beach, Calif.

[73] Assignee: Thoro-Ray Inc., Fort Worth, Tex.

[21] Appl. No.: 811,160

[22] Filed: Jun. 29, 1977

Related U.S. Application Data

[63] Continuation-in-part of Ser. No. 672,608, Apr. 1, 1976, abandoned.

[51] Int. Cl.² .............................................. H01J 35/00
[52] U.S. Cl. ................................... 250/490; 250/402; 250/439 P; 250/515
[58] Field of Search .................. 250/404, 490, 439 P, 250/399, 515, 520, 402; 313/55, 57

[56] References Cited

U.S. PATENT DOCUMENTS

| 1,881,448 | 10/1932 | Forde et al. | 250/399 |
| 1,946,287 | 2/1934 | Kearsley | 250/399 |
| 2,531,583 | 11/1950 | Ott | 250/439 P |
| 2,946,892 | 7/1960 | Bas-Taynaz | 250/439 P |
| 3,359,423 | 12/1967 | Koerner et al. | 250/399 |
| 3,906,235 | 9/1975 | Fischer | 250/404 |

Primary Examiner—Alfred E. Smith
Assistant Examiner—B. C. Anderson
Attorney, Agent, or Firm—William W. Haefliger

[57] ABSTRACT

Dental X-ray apparatus characterized by very substantial reductions in radiation exposure of the patient, comprises:
(a) X-ray tube means providing an electron beam,
(b) a beam target carried by said means and located axially rearwardly thereof to be received rearwardly into a patient's mouth,
(c) the target angled relative to the said axis to produce a radiation pattern that extends forwardly of the target and also rearwardly and sidewardly of the target, said X-ray tube means including structure to cause the electron beam to form a beam impingement spot on the target of sufficiently small size that radiation emanating from said spot and directed toward a tooth and film produce a sharp boundary tooth image on the film, and
(d) an X-ray absorbing shield adjacent the target rearwardly thereof and extending forwardly at the side of the target, the shield and target being integrally connected, the shield defining a probe that projects rearwardly for reception into the patient's mouth.

19 Claims, 11 Drawing Figures

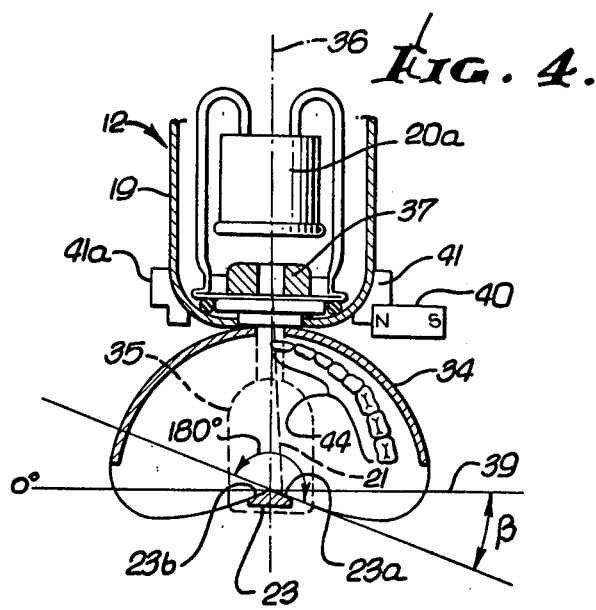
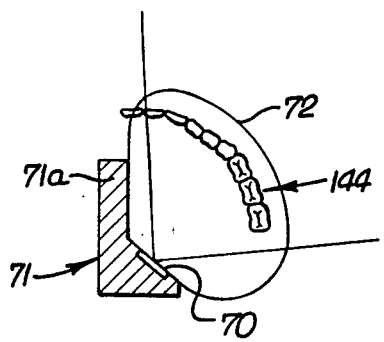
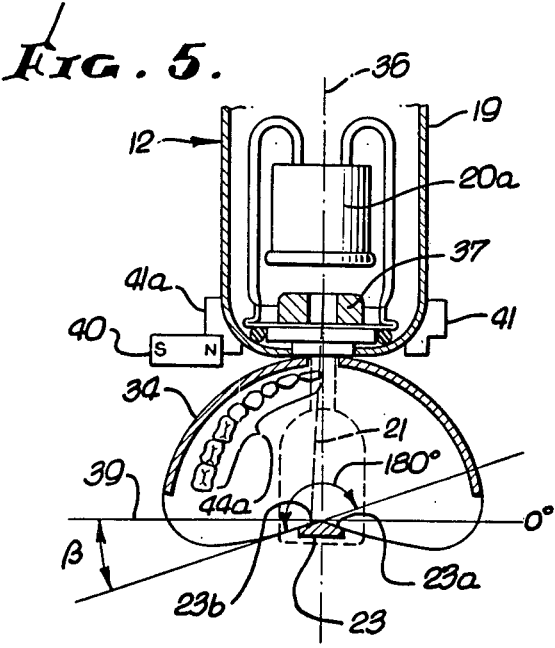
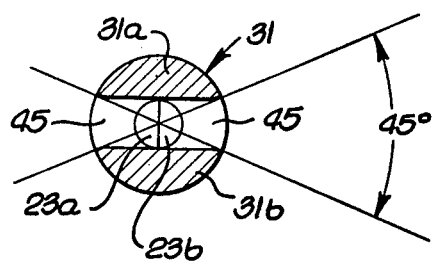
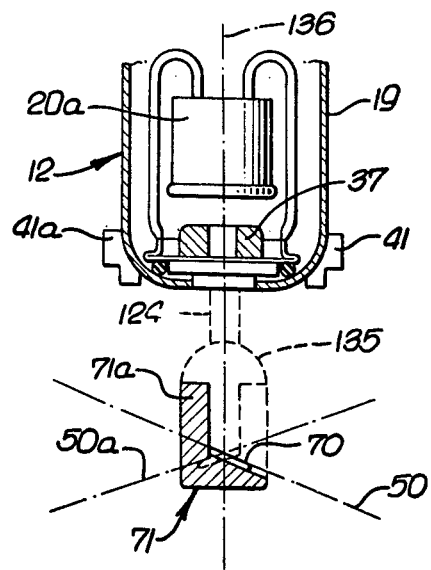

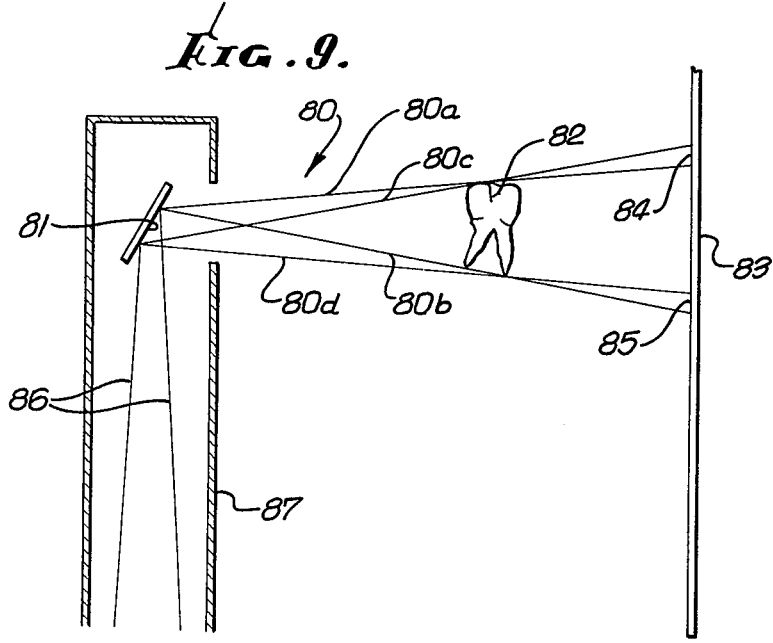
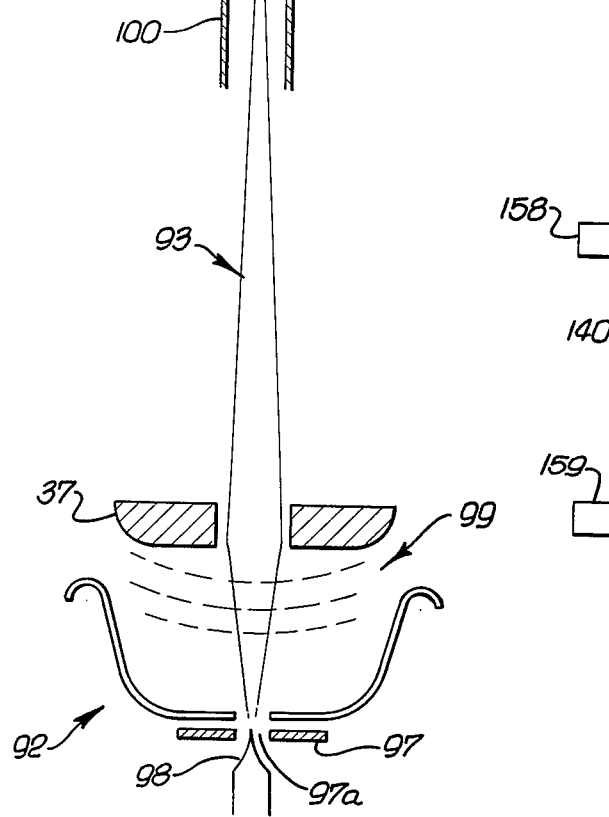
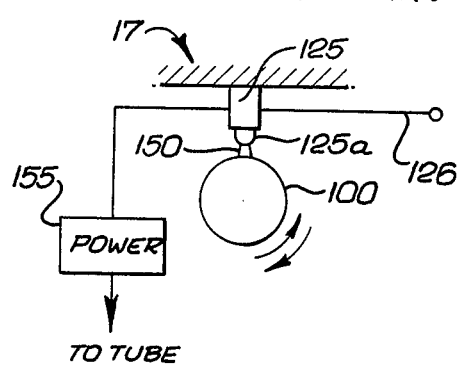
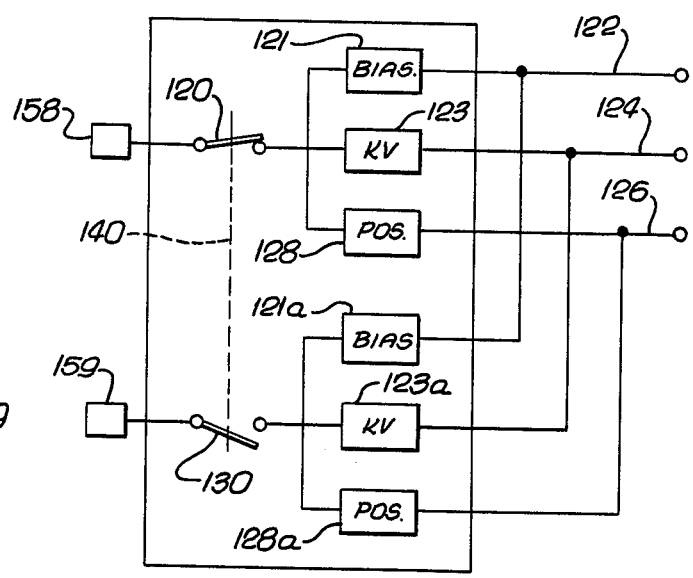

DENTAL AND MEDICAL X-RAY APPARATUS

BACKGROUND OF THE INVENTION

This application is a continuation-in-part of my earlier application Ser. No. 672,608 filed Apr. 1, 1976 and entitled "Dental and Medical X-Ray Apparatus", abandoned.

This invention relates generally to X-ray apparatus and techniques; more particularly, it concerns method and equipment enabling rapid X-ray examination of teeth, with substantially reduced exposure to radiation.

Present systems of X-ray examination of human teeth require up to eighteen exposures, accompanied by objectionably excessive amounts of side radiation to sensitive areas of the brain, cortex, sinus, throat, optic and auditory nerve centers. Recently, a technique has been proposed according to which an X-ray target is introduced into the mouth, and radiation is directed from the target back through the teeth to film supported outside the mouth, thereby to produce a so-called high resolution, panoramic radiograph. One problem encountered with that type equipment concerns the tendency to produce gagging of the patient, due to the necessity of locating the target sufficiently close to the throat that back teeth will be exposed to produced X-rays. Another problem has to do with the requirement that the upper and lower teeth be alternately exposed to radiation, which in turn requires that the shield associated with the target be re-arranged. This means that the target is removed from the oral cavity after the first exposure (as for example irradiation of the upper teeth, after which the target is re-introduced to enable the second exposure (of the lower teeth) which increases the risk of gagging and otherwise discomfort the patient.

SUMMARY OF THE INVENTION

It is a major object of the invention to provide improvements in technique and apparatus which will overcome the above objects and disadvantages. Another object is to provide target and shield configurations within the oral cavity whereby gagging will be eliminated, and all of the front and rear teeth will be irradiated, while flat upper and lower portions of the mouth and sensitive areas of the head will not be unintentionally exposed to X-rays.

Basically, the invention is embodied in apparatus that includes:

(a) X-ray tube means providing an electron beam, (b) a beam target carried by said means and located axially rearwardly thereof to be received rearwardly into a patient's mouth, (c) the target angled relative to said axis to produce a radiation pattern that extends forwardly of the target and also rearward and sidewardly of the target, the beam forming a microfocal spot on the target, and (d) a shield extending forwardly above and below the target and also rearwardly thereof.

As will be seen, the shield projects forwardly both above and below the target to block radiation from passing to undesirable areas of the patient's head zones above the upper teeth and below the lower teeth; the shield may typically provide lateral openings to pass X-rays toward the back upper and lower teeth; the target may typically be angled rearwardly and sidewardly at one or both sides of the equipment axis so that radiation may pass through one or both of the shield side openings to provide access to the back teeth as well as front teeth; the microfocal spot is sufficiently small that the image of a tooth on X-ray film has a sharp boundary; and the radiation pattern produced by the target may be transversely shifted, as for example by sideward deflection of the beam to strike different portions of the target, or by physical rotation of the target, so that the target need not be removed from the mouth between exposures.

Another object concerns the provision of method and means to vary the size of the beam impingement spot on the target, for purposes as will appear.

These and other objects and advantages of the invention, as well as the details of illustrative embodiments, will be more fully understood from the following description and drawings, in which:

DRAWING DESCRIPTION

FIGS. 4 and 5 are top plan views of gun and target relationships, in schematic form;

FIG. 6 is an enlarged frontal view of the target and shield;

FIG. 7 is a view like FIG. 4 in FIG. 5, but showing an alternative target; and FIG. 8 shows another target;

FIG. 9 is a diagram of X-ray interception by a tooth and film;

FIG. 10 is another diagram of X-ray generation at a microfocal spot on a target, and X-ray interception by a tooth and film, and FIG. 11 is a circuit diagram.

DETAILED DESCRIPTION

Figure 1:
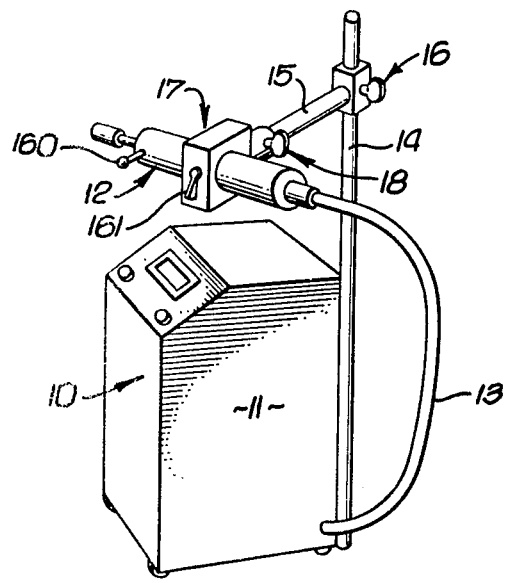
FIG. 1 is a perspective showing of high voltage generator equipment and X-ray tube floor mount associated with the invention.

Referring first to FIG. 1, x-ray apparatus 10 includes a high voltage generator console 11 to which X-ray tube 12 is electrically connected, as via cable 13. A suitable adjustable support for the tube 12 includes upright post 14 carried by the console; an arm 15 adjustably attached at 16 to the post to rotate about a vertical axis; and a mount 17 for the tube apparatus and adjustably attached at 18 to the arm 15 to rotate or swivel about a horizontal axis.

Figure 2:
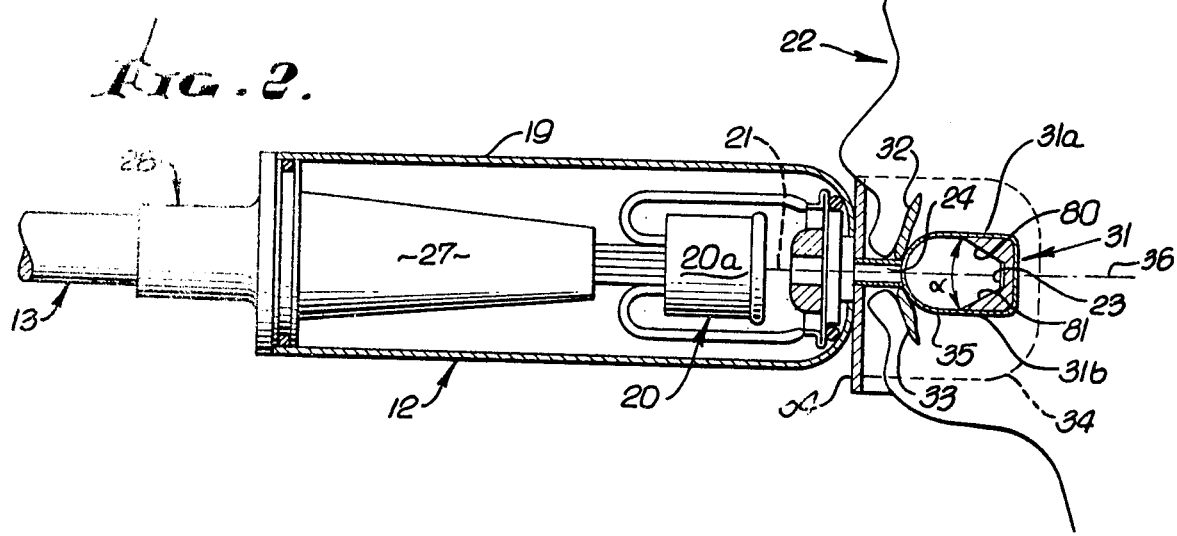
FIG. 2 is a cross sectional view of gun and target apparatus embodying the invention.

Extending the description to FIG. 2, the tube means 12 includes a housing 19 containing the micro-focus X-ray tube 20 which produces an electron beam 21. A beam target 23 is carried by the tube means and is located axially rearwardly thereof (relative to the patient's head 22) to be inserted or received relatively rearwardly into the patient's mouth. The forward and rearward axis appears at 36. In the example shown, the target 23 is carried by the rearward end portion of a rearwardly axially elongated tubular element 24 projecting into the patient's mouth. The cable 13 is attached to the housing at 26, and passes through an insulator 27 to the gun 20a. The inner conductor of the cable is at high potential while the outer cable sheath is at ground potential and is solidly connected to the tube housing. The tube anode is also at ground potential and only the electron gun 20a is at high potential, insulated by gas or oil inside the tube housing. This provides the necessary electrically shock-proof mounting for intraoral radiography.

Figure 3:
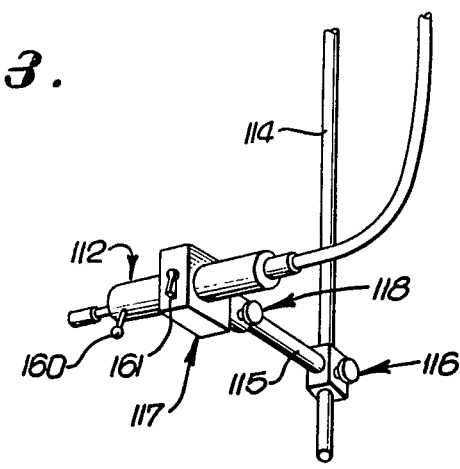
FIG. 3 is a perspective showing of an alternative X-ray tube ceiling mounting.

An alternative ceiling mount for the tube 112 in FIG. 3 includes an upright post 114 affixed to or carried by the ceiling of a room. Elements 115–118 correspond to elements 15–18 in FIG. 1.

The target 23 may consist of tungsten embedded in a copper shield 31, the latter having upper and lower rearwardly tapering surfaces 80 and 81 which define an angle α therebetween. That angle subtends a zone which encompasses the patient's upper and lower teeth (including root areas) indicated at 32 and 33, but not including undesirably irradiated areas, the latter as well as the throat being protected from radiation impingement. In this regard, an X-ray film holder 34 is carried by the apparatus 12 to extend at the front of the patient's mouth, and to overlap his cheeks at opposite sides of the mouth. The film holder is also substantially subtended by the angle α. The target and shield are carried by the anode envelope 35 with is in turn carried by the tubular element 24. The anode envelope material is a low X-ray absorbtion material such as beryllium, titanium or aluminum, and forms the window for radiation emission. Another such window material is ceramic, as for example beryllium oxide, aluminum oxide, or combination of same with up to 20% by weight of silicon dioxide as a vitreous fluxing material.

Extending the description to FIG. 4, the tube anode 37 is shown axially rearwardly of the gun 20a. The target 23, located axially rearwardly of the anode, has surfaces 23a and 23b angled rearwardly and transversely (i.e. sidewardly) relative to the axis 36. Surfaces 23a and 23b are transversely symmetrical relative to axis 36, and taper axially forwardly, as shown, at angles β relative to an upright plane 39 normal to axis 36; angle β may for example be about 20°.

In accordance with an important aspect of the invention, means is provided to effect transverse shifting of the radiation pattern produced in response to beam incidence on the target. Such means may comprise a magnet supported to be shifted transversely to deflect the beam transversely relative to the target; for example, FIG. 4 shows the magnet 40 suitably supported at 41 by the tube at the right side of the axis 36, and rearwardly of the anode 37, the magnet acting to deflect the beam 21 transversely rightwardly so that it impinges on surface 23a. As a result, X-rays are produced to travel forwardly through the upper and lower teeth and face at the right side of the patient's mouth and to the film in holder 34, such teeth indicated at 44. Actually, radiation may extend transversely over the 180° angle indicated, and defined by the plane of surface 23a, and the shield does not interrupt such sideward radiation. See in this regard the shield openings 45 at opposite sides of the target, in FIG. 6. Accordingly, the shield has sections 31a and 31b above and below the target.

Upon completion of exposure of the right side teeth 44 to X-radiation, the magnet 40 is transversely shifted to the left side of axis 36, i.e. to a position as for example appears in FIG. 5. In that position, suitably supported at 41a by the tube, the magnet acts to deflect the beam 21 transversely leftwardly, so that it impinges on target left surface 23b. As a result, X-rays are produced to travel forwardly through the patient's upper and lower teeth and face at the left side of the mouth, and to the film in the holder 34, such teeth indicated at 44a. Here again, radiation may extend transversely over the 180° angle indicated and defined by the plane of surface 23b. The shield does not interrupt such sideward radiation, but does limit radiation in upper and lower directions, to remain within the angle α previously described.

Holders 41 and 41a may suitably releasably retain the magnet, as by detents. If desired, the magnet 40 may be rotatably carried to swing about axis 36 between the positions seen in FIGS. 4 and 5.

FIG. 7 shows an alternative means to effect transverse shifting of the X-ray pattern with a fixed target, seen in FIG. 8. In this view, the tube 12 and supported target 70 are rotatable about axis 136 between the solid line and broken line target surface positions shown in 50 and 50a. For example, in FIG. 1 the mount 17 may incorporate means to rotatably support the tube 12 to rotate about axis 136. A sidewardly projecting handle to rotate the tube 180° outside the mouth appears at 160. A tube position locking toggle appears at 161. In target position 50, the operation corresponds to that described in FIG. 4; whereas in target position 50a, the operation corresponds to that described in connection with FIG. 5. Envelope 135 and support element 124 corresponds to items 35 and 24 in FIG. 2.

FIG. 8 shows the modified tungsten target 70 supported by shield 71, the latter projecting forwardly at 71a sidewardly of the target to block X-ray sideward travel and confine same to the region 72. The latter is related to teeth 144 at one side of the mouth, as shown. Portions of the copper shield 71 not shown extend above and below the target and forwardly as in FIG. 6, so that a side opening is formed at only one side of the target. Target 70 and shield 71 rotate with the tube, as explained above.

It should be pointed out that since the X-ray intensity necessary for the required film density is proportional to the square of the focus-to-film distance, the radiation output of the X-ray source at 5cm need be only 1/25 or 4% of that required at 25cm with the conventional extra-oral X-ray tube distance.

The wide-angle radiation pattern of the present tube can expose a panoramic view of half the mouth including upper and lower teeth in one exposure, so that only two X-ray pictures are necessary instead of 18 with conventional extra-oral tubes. When this correction is included in the 4% noted above, the total reduction in radiation amounts to only 0.66% of that required with conventional dental radiography for the same visual information. This is a very significant reduction in radiation dosage which is less than 1% of the present radiation level for whole-mouth dental radiography. In addition, the integral connection of the probe shield and target enables grounding of the target and probe for shockproof use, and without need for coolant jacketing.

Referring to FIG. 9, it shows an unimproved means for generating an X-ray beam 80 at an elongated target region 81. X-rays 80a and 80b emanate from one end of region 81 to encompass the tooth 82, and X-rays 80c and 80d emanate from the opposite end of region 81 to encompass the tooth. The tooth boundary is not sharply delineated at the film 83, there being shadowy regions 84 and 85 at the film between rays 80a and 80c, and between rays 80b and 80d, respectively. The electron beam directed at the target is indicated at 86, within probe 87.

FIG. 10 shows an improved means for generating an X-ray beam 90 at a microfocal spot at target 91. The tube means, indicated at 92, includes structure (as for example focussing anode 37) to cause the electron beam 93 to converge and form the beam impingement microfocal spot, of sufficiently small size that X-radiation 90 is directed toward the tooth 94 and film 95 to produce a sharp boundary tooth image 96 on the film. The "spot" 91 may have an overall maximum cross-dimension of between about 0.05 and 0.10 millimeters, to produce the sharp boundary tooth image. Note the X-rays 90a and 90b encompassing the tooth and appearing to emanate from a point source at the target. A figure of merit for the reduction of geometric unsharpness $U_g$ is directly related to focal spot size $f_s$ and image magnification M as follows:

$$U_g = f_s(M-1)$$

where M = focus to film distance ÷ focus to subject distance.

The tube means 92 also typically includes a forming electrode 97 having a central opening 97a into which electron emitting filament 98 projects. The electron beam is precisely converged by the electrostatic field (see broken line 99) produced by anode 37, and resulting in a simple convergent "lens effect". A high beam "perveance" ($I = V^{3/2}$), i.e. electron flux up to 3 milliamperes, also results, with better image production at the film. The probe 100 may be narrow and hence less objectionable in patient's mouth due to the converging of beam 93, and also due to the absence of any need for a coolant jacket about the single wall probe. A window 101 carried by the probe may consist of ceramic material, or other material, as described above, to pass the X-ray beam 90.

FIG. 11 schematically shows circuit means to adjust the bias on the anode 37, and hence the electrostatic field strength and the size of spot 91; the power (KV) applied to the beam; and the operation of a microswitch which controls energization of the X-ray tube. For example, if push-button switch 120 is operated as for example for intra-oral mode use of the probe, the bias source 121 may energized to a level say of about −50 volts appearing on lead 122 connected to electrode 37 (whereby the size of spot 91 is then about 0.1 mm, for example); the "power" source 123 may be energized to a level say of about 50 KV applied via lead 124 to the gun; and the position control circuit 128 of microswitch 125 is completed via lead 126. The microswitch is then activated to effect power application (see power source 155) to the X-ray tube only if the probe 100 has been rotated (see arrows) so as to direct the X-ray beam toward teeth or other zones which are not "undesired", i.e. radiation is then blocked by the shielding, as described, from passing to undesired areas of the patient's head zones.

On the other hand, if push-button switch 130 is operated, as for example for extra-oral mode use of the probe to provide dental X-rays (with film then in the patient's mouth), the bias source 121a may be energized to a level say of −25 volts (whereby the size of the spot is increased to about 0.3 mm for example); the "power" source 123a may be energized to a level say of about 70–90 KV; and the position control circuit 128a of the microswitch 125 is then deactivated, so that the X-ray tube is powered in any rotary position of the probe, as during extra-oral operation. The increased size of the spot is then no problem since the probe and target are normally located at sufficient distance from the patient's face to obviate shadowing.

Microswitch 125 may be carried by the mount 17. The probe 24 may carry a button 150 to engage and displace the microswitch element 125a, on rotation of the probe to the position shown.

The push-button switches 120 and 130 may be gang connected as at 140 so that closing of switch 120 opens switch 130 to deactivate sources 121a, 123a and 128a; and closing of switch 130 opens switch 120 to deactivate sources 121, 123 and 128. See also power sources 158 and 159. The circuitry of FIG. 11 is schematic, and variations and refinements can of course be made all within the scope of the inventive intent.

It is therefore seen that provision is made to increase power to the tube and increase spot 91 size (preventing pitting or eroding of the target at high beam current densities) for exta-oral operation.

I claim:

1. In dental X-ray apparatus
   (a) X-ray tube means providing an electron beam,
   (b) a beam target carried by said means and located axially rearwardly thereof to be received rearwardly into a patient's mouth,
   (c) the target angled relative to said axis to produce a radiation pattern that extends forwardly of the target and also rearwardly and sidewardly of the target, said X-ray tube means including structure to cause the electron beam to form a beam impingement spot on the target of sufficiently small size that radiation emanating from said spot and directed toward a tooth and film produce a sharp boundary tooth image on the film, and
   (d) an X-ray absorbing shield adjacent the target rearwardly thereof and extending forwardly at the side of the target, the shield and target being integrally connected, the shield defining a probe that projects rearwardly for reception into the patient's mouth.

2. The apparatus of claim 1 wherein the target has surface planar flatness and is angled rearwardly and transversely relative to said axis to face forwardly and toward only one side of the probe.

3. The apparatus of claim 1 wherein the target is tapered axially forwardly.

4. The apparatus of claim 2 wherein the shield forms one side opening toward which said target surface faces.

5. The apparatus of claim 4 wherein the shield consists of copper, and the target consists of tungsten.

6. In dental X-ray apparatus
   (a) X-ray tube means providing a beam of electrons,
   (b) a beam target carried by said means and located axially rearwardly thereof to be inserted rearwardly into a patient's mouth,
   (c) the target angled relative to said axis,
   (d) means to effect transverse shifting of the radiation pattern produced in response to beam incidence on the target, and
   (e) an X-ray absorbing shield projecting forwardly at the side of the target and forming an opening at one side thereof, the shield and target being integrally interconnected, the shield defining a probe that projects rearwardly for reception into the patient's mouth.

7. The apparatus of claim 1 wherein said means comprises a magnet supported to be shifted transversely to deflect the beam transversely relative to the target.

8. The apparatus of claim 1 wherein said means comprises structure to displace the target surface angularity relative to said axis.

9. The apparatus of claim 6 wherein the target has two surfaces that taper axially forwardly at opposite sides of the tube axis and symmetrically thereto.

10. The apparatus of claim 6 wherein the target has surface planar flatness and is angled transversely and rearwardly and produces a radiation pattern that extends forwardly of the target and also rearwardly and sidewardly of the target, the target facing forwardly and toward only one side of the probe, the probe having only one wall and being free of coolant jacketing.

11. The apparatus of claim 6 wherein said means includes a rearwardly axially elongated tubular element on the rearward end portion of which said target is carried, said element having only a simple wall.

12. The apparatus of claim 11 including an X-ray film holder carried by said apparatus to extend at the front of the patient's mouth and to overlap the patient's cheeks at opposite sides of the mouth.

13. In dental X-ray apparatus,
(a) X-ray tube means providing an electron beam,
(b) a beam target carried by said means and located axially rearwardly thereof to be received rearwardly into a patient's mouth, said X-ray tube means including structure to cause the electron beam to form a beam impingement spot on the target of sufficiently small size that radiation emanating from said spot and directed toward a tooth and film produce a sharp boundary tooth image on the film,
(c) and an X-ray absorbing shield adjacent the target rearwardly thereof, the shield projecting forwardly both above and below the target to block radiation from passing to undesirable areas of the patient's head zones above the upper teeth and below the lower teeth, the shield providing a sideward opening to pass radiation toward the back upper and lower teeth, the shield and target being integrally connected, the shield defining a probe that projects rearwardly for reception into the patient's mouth.

14. The apparatus of claim 1 including a side window at one side of the shield, said window consisting of a low X-ray absorption material.

15. The apparatus of claim 14 wherein said window consists of ceramic material.

16. The apparatus of claim 1 wherein said structure includes control means for controlling said beam to selectively increase the size of said spot at the target.

17. The apparatus of claim 16 wherein said control means includes manually controllable switch means having a first position in which power application to the tube is at a relatively lower level and said spot is of relatively smaller size, and a second position in which power application to the tube is at a relatively higher level and said spot is of relatively larger size.

18. The apparatus of claim 17 including additional control means to prevent power application to the tube when said switch means is in said first position and said shield is out of selected position relative to the patient's head.

19. The method of operating dental X-ray apparatus which includes:
(a) X-ray tube means providing an electron beam,
(b) a probe receivable rearwardly in a patient's mouth, and carrying a beam target, the probe having an X-ray passing window and shielding for said target,
(c) said tube means including control structure to control the size of the beam impingement spot on the target, said method including the steps:
(d) operating said structure to produce a relatively small size spot at the target in conjunction with operation of said apparatus with said probe in the mouth of a patient, and
(e) operating said structure to produce a relatively larger size spot at the target in conjunction with operation of said apparatus to produce dental X-rays with said probe located outside the mouth of a patient but with said X-rays directed at the mouth,
(f) and, during said operation of said structure, maintaining said shielding adjacent the target rearwardly thereof and extending forwardly at the side of the target, and maintaining the shield and target integrally connected.

* * * * *